United States Patent [19]
Butterfield et al.

[11] 4,071,632
[45] Jan. 31, 1978

[54] METHOD OF ALLEVIATING HYPERTENSION

[75] Inventors: James L. Butterfield, New Berlin; George C. Wright, Norwich, both of N.Y.

[73] Assignee: Morton-Norwich Products, Inc., Norwich, N.Y.

[21] Appl. No.: 755,457

[22] Filed: Dec. 30, 1976

[51] Int. Cl.$^2$ .............................................. A61K 31/44
[52] U.S. Cl. .................................................... 424/263
[58] Field of Search ........................................ 424/263

[56] References Cited
PUBLICATIONS
Lewis et al –Chem. Abst., vol. 74, (1971) p. 112022t.

Primary Examiner—Sam Rosen
Attorney, Agent, or Firm—Anthony J. Franze

[57] ABSTRACT

3-Amino-2-hydrazinopyridine hydrochloride is useful in the alleviation of hypertension.

1 Claim, No Drawings

METHOD OF ALLEVIATING HYPERTENSION

This invention is concerned with the treatment of hypertension. More particularly, it is concerned with a method of treating hypertension by the administration of 3-amino-2-hydrazinopyridine hydrochloride to a hypertensive host.

The compound 3-amino-2-hydrazinopyridine hydrochloride has been described in U.S. Pat. No. 3,549,631.

It has now been discovered that 3-amino-2-hydrazinopyridine hydrochloride when administered intraperitoneally, intravenously or orally to spontaneously hypertensive rats in a dose ranging from 0.1 to 100 mg/kg in a vehicle such as isotonic saline produced marked reduction in arterial blood pressure. The magnitude and duration of the antihypertensive effect elicited by this compound is dose dependent, lower dosages causing less and shorter time period reduction of blood pressure and larger dosages increasing the amount and time period of blood pressure lowering.

Suitable pharmaceutical forms for administration of 3-amino-2-hydrazinopyridine hydrochloride comprise those commonly employed dosage formulations such as tablets, solutions, suspensions and capsules using commonly employed-excipients and adjuvants, such forms containing from 10-500 mg of the compound per unit dosage form.

What is claimed is:

1. A method for alleviating hypertension which comprises administering to a hypertensive host an antihypertensive amount of 3-amino-2-hydrazinopyridine hydrochloride in acceptable pharmaceutical dosage form.

* * * * *